(12) United States Patent
Newman

(10) Patent No.: US 9,759,642 B2
(45) Date of Patent: Sep. 12, 2017

(54) METHOD AND SYSTEM FOR MEASURING A PROPERTY OF A NON-NEWTONIAN FLUID

(71) Applicant: John W. Newman, Newtown Square, PA (US)

(72) Inventor: John W. Newman, Newtown Square, PA (US)

(73) Assignee: John W. Newman, Norristown, PA (US)

( * ) Notice: Subject to any disclaimer, the term of this patent is extended or adjusted under 35 U.S.C. 154(b) by 105 days.

(21) Appl. No.: 13/936,893

(22) Filed: Jul. 8, 2013

(65) Prior Publication Data

US 2014/0007658 A1    Jan. 9, 2014

Related U.S. Application Data

(60) Provisional application No. 61/668,704, filed on Jul. 6, 2012.

(51) Int. Cl.
*G01N 11/06* (2006.01)
*G01N 11/00* (2006.01)
(Continued)

(52) U.S. Cl.
CPC ............. *G01N 11/00* (2013.01); *G01N 11/06* (2013.01); *G01N 33/26* (2013.01); *G01N 33/42* (2013.01);
(Continued)

(58) Field of Classification Search
CPC ..................................................... G01N 11/06
(Continued)

(56) References Cited

U.S. PATENT DOCUMENTS 5,005,401 A    4/1991 Pierce et al.
5,024,080 A    6/1991 Backes

FOREIGN PATENT DOCUMENTS

JP    2009-85639    4/2009
WO    2006/110963 A1    10/2006

OTHER PUBLICATIONS

Search Report and Written Opinion from corresponding International Application PCT/US2013/049591.
(Continued)

*Primary Examiner* — Peter Macchiarolo
*Assistant Examiner* — Alexander Mercado
(74) *Attorney, Agent, or Firm* — Ice Miller, LLP

(57) ABSTRACT

A system and method for measuring the deformation over time of the surface of a non-Newtonian fluid in a sampling container in response to an airjet that is applied for a specified time. The change is the sample surface displacement is measured quantitatively by means of optical triangulation or other similar optical or electronic distance measuring device. After cessation of the airjet, gravitational forces cause the sample material to flow back to its original surface profile. Both the amplitude of the deformation displacement due to the force of the airjet and the recovered displacement, within specific time periods are characteristic of asphalt binder material with varying amounts of polymer or other additives used to control the ultimate properties and performance of the material. As a result, comparison of the quantitative measurements of control samples can allow discrimination from samples with different properties and hence different formulations.

19 Claims, 4 Drawing Sheets

(51) Int. Cl.
*G01N 33/42* (2006.01)
*G01N 33/26* (2006.01)

(52) U.S. Cl.
CPC ............... *G01N 2203/0044* (2013.01); *G01N 2203/0094* (2013.01)

(58) Field of Classification Search
USPC ....................................................... 73/51.14
See application file for complete search history.

(56) References Cited

OTHER PUBLICATIONS

Office Action issued Jan. 26, 2017 in CA Application No. 2,878,507.

METHOD AND SYSTEM FOR MEASURING A PROPERTY OF A NON-NEWTONIAN FLUID

This is a nonprovisional of U.S. Provisional Application Ser. No. 61/668,704, filed Jul. 6, 2012, the entire disclosure of which is hereby incorporated by reference as if set forth fully herein.

BACKGROUND OF THE INVENTION

1. Field of the Invention

This invention relates generally to the field of material testing, and more specifically to a method and system for measuring properties of a non-Newtonian fluid, such as an asphalt binder.

2. Description of the Related Technology

The word asphalt generally refers to any one of a number of different viscous bituminous substances that can be used for paving or road making The viscous asphalt material is typically used to bind aggregate materials such as crushed stone in order to form a paved surface.

Thermal shrinkage cracking in asphalt pavement occurs when the thermal tensile stress within the asphalt pavement that results from temperature drop exceeds the strength at that temperature. Historically, low temperature thermal cracks have been controlled by limiting the asphalt binder stiffness. Assuming similar asphalt binder tensile strengths and coefficients of thermal expansion/contraction, the binders with a higher stiffness will crack at a higher temperature than softer binders. Because an accurate and easy to use measuring instrument was not available, the cracking temperature or the limiting low temperature stiffness of asphalt binder had been extrapolated from consistencies measured at higher temperatures, such as penetrations at 5 and 25° C., viscosity at 25° C., or ring-and-ball softening point (50-60° C.). Hill, J. F., Inst. Petroleum, vol. 74-014 (1974) and Van der Poel, C., Journal of Applied Chemistry, vol. 4, 221-236 (1954).

In the United States, the Association of American State Highway and Transportation Officials (AASHTO) has published and implemented a series of performance graded ("PG") binder specifications. Low-end temperatures of PG grading are typically determined by utilizing one or more of several known systems including the Bending Beam Rheometer (BBR) and/or the Direct Tension Tester (DTT). While effective at generating useful data, these systems are complex, require the performance of numerous calculations, require the testing of many specimens, do not directly measure the temperature at which the specimen fails, and are often very time consuming and expensive to perform.

A need accordingly exists for a system and method for measuring the properties of a non-Newtonian fluid that is less time-consuming and expensive than conventional systems and methods.

SUMMARY OF THE INVENTION

Accordingly, it is an object of the invention to provide a system and method for measuring the properties of a non-Newtonian fluid that is less time-consuming and expensive than conventional systems and methods.

The present invention measures the deformation over time of the surface of a non-Newtonian fluid in a sampling container in response to an airjet applied for a specified time. The change is the sample surface displacement is measured quantitatively by means of optical triangulation or other similar optical or electronic distance measuring device. After cessation of the airjet, gravitational forces cause the sample material to flow back to its original surface profile. Both the amplitude of the deformation displacement due to the force of the airjet and the recovered displacement, within specific time periods are characteristic of asphalt binder material with varying amounts of polymer or other additives used to control the ultimate properties and performance of the material. As a result, comparison of the quantitative measurements of control samples can allow discrimination from samples with different properties and hence different formulations.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

The embodiments of the present invention comprise components and method for making quantitative measurements of the deformation of the surface of a non-Newtonian fluid over time in order to discriminate samples with varying properties. Various air jet tube configurations yield similar results, the objective being to create a flow of air emanating from a tube or nozzle that retains its cross sectional velocity profile for a working distance from the tube or nozzle end point to the surface of the sample being tested. Further, best results are obtained when the center of the air jet is coincident with the center of the measuring laser beam from the laser based displacement sensor.

If the angle between the airjet and the laser beam is substantially greater than zero degrees, the airjet and the laser will be coincident at substantially only one point in space, the coincident point, requiring the sample container to be adjusted in height until the plane of the sample surface contains the coincident point.

Figure 3:
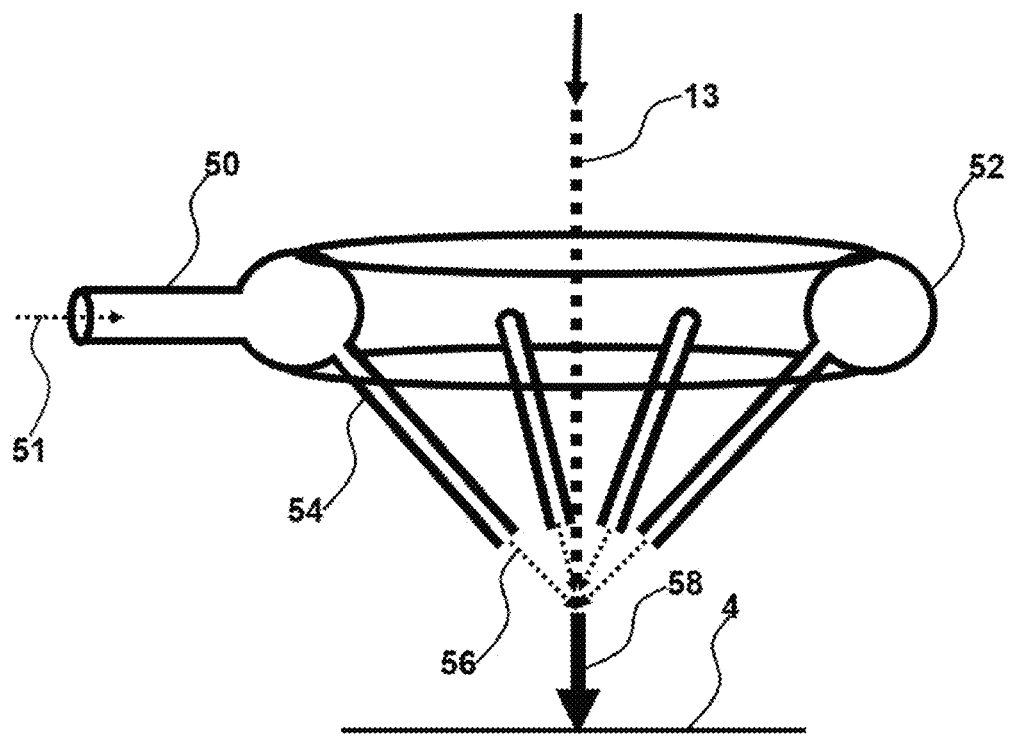
FIG. 3 shows a manifold with a plurality of tubes for directing air to a single convergent point in space to create a single linear jet of air with a uniform pressure over a variable working distance that is substantially coaxial with the laser beam or other sensing medium used to measure sample surface displacements.
Figure 4:
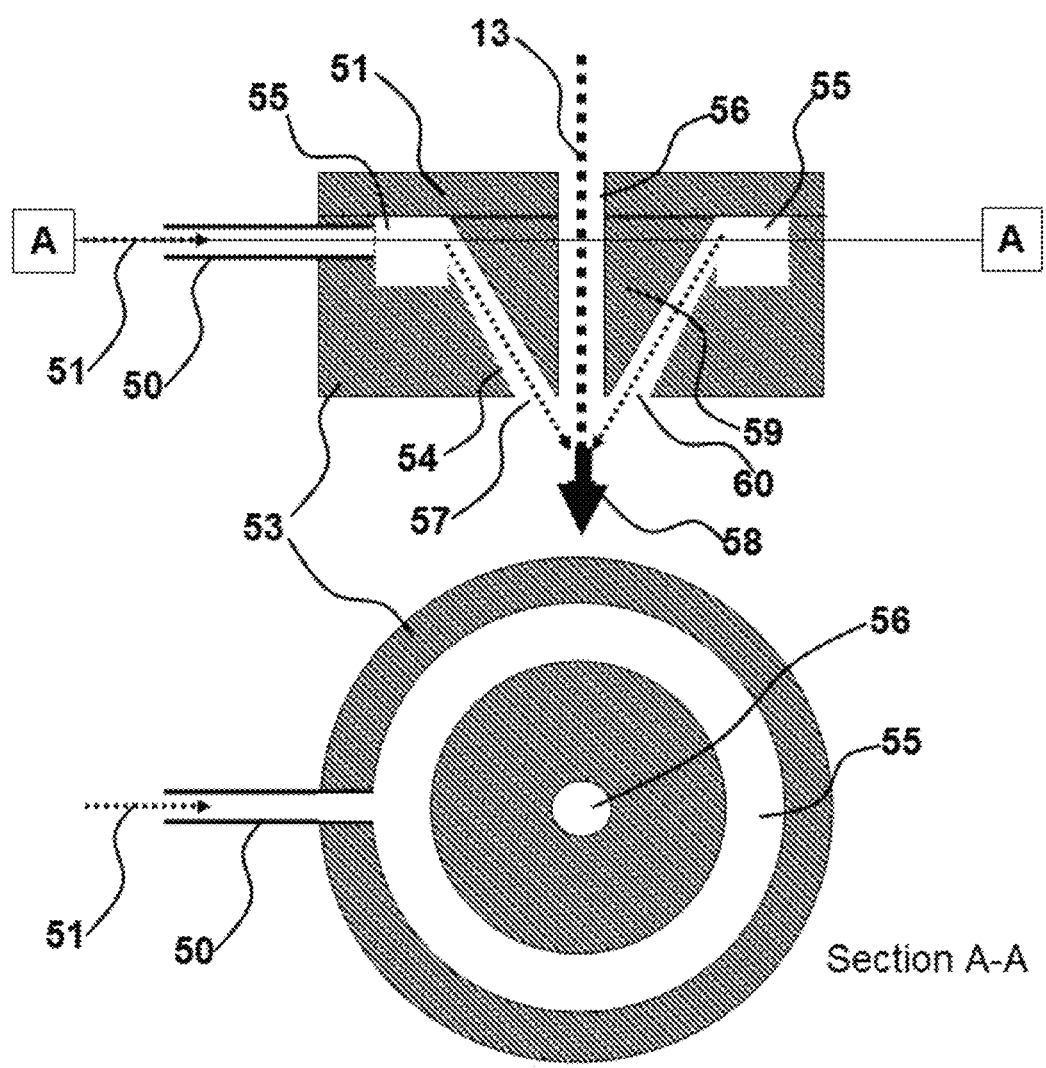
FIG. 4 shows another device configuration using a convergent conical cavity to generate a single linear jet of air with a uniform pressure over a variable working distance that is substantially coaxial with the laser beam or other sensing medium used to measure sample surface displacements.

Using a plurality of tubes or nozzles as shown in FIG. 3, or a conical nozzle as shown in FIG. 4 air can be directed to combine into a substantially single jet of air with an approximately constant pressure cross section over a working distance of up to several inches. This allows for a simplified sample holder and reduces the need for precise adjustments to the sample container height. The system operates by applying an airjet to the sample surface, creating a force of that deforms the sample surface. Samples that have a low viscosity may be tested with a lower jet pressure to keep the deformation within the range of the displacement measuring device. A load cell may be included to measure the force of the airjet on the sample during test. The system can then use the force measurement to control the airflow so repeatable applications of force are applied to samples regardless of the air temperature, altitude and air pressure at the location where the tests are conducted.

Figure 1:
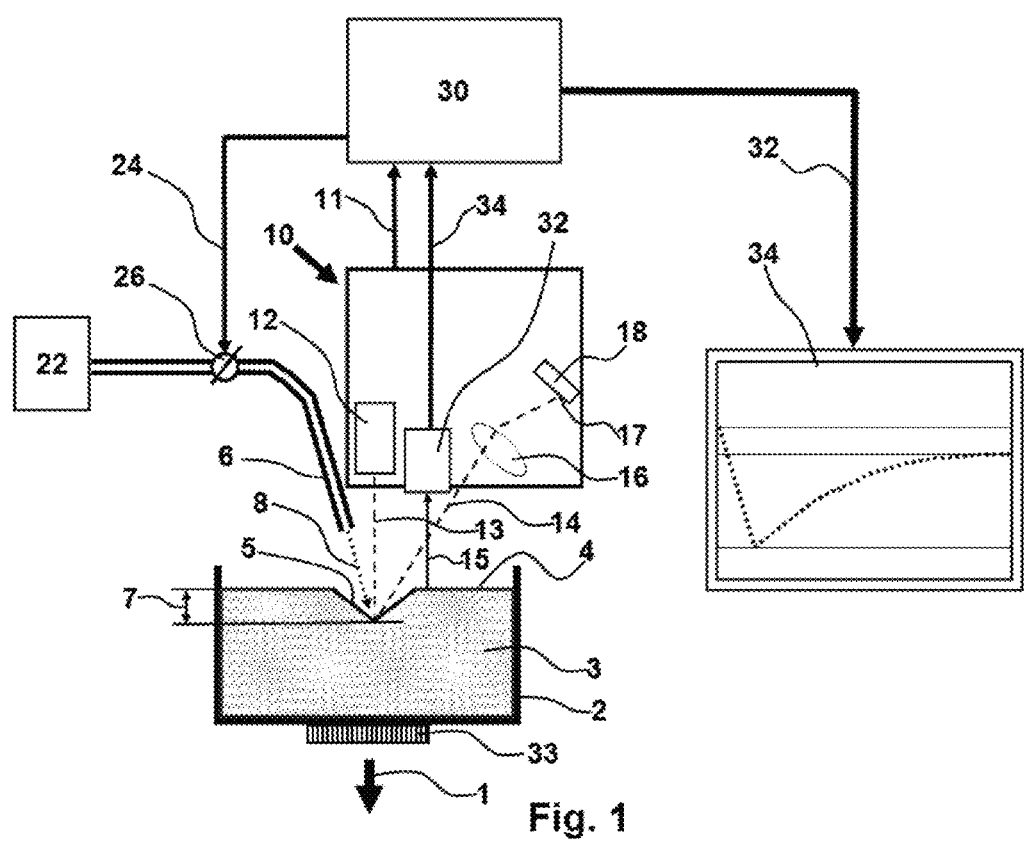
FIG. 1 is a schematic diagram of the device for measuring characteristics of non-Newtonian fluids showing the key components in accordance with an embodiment of the invention.

FIG. 1 shows a schematic diagram for a system for screening asphalt binder material to determine the presence of the expected constituent ingredients prior to the construction or maintenance of road surfaces. This device specifically measures the sample surface deformation in response to an applied force and the changes in surface displacement during a recovery period after the air jet is turned off.

The system consisting of the following components and features. The force of gravity "g" 1 causes the surface 4 of asphalt binder sample 3 with mass (m) held in container 2 to become level over time. Once level, the container 2 is placed in a position such that both the laser beam 13 from the laser distance measuring device 10 and the off axis air jet 8 from tube 6 meet on the surface 4 of the asphalt binder material 3. The air jet may be formed by a single tube and impinge on the surface 4 at an angle. If a greater working distance range is desired, the use of multiple tubes as shown in FIG. 3 or a series of orifices in a ring manifold or a conical annular nozzle as shown in FIG. 4, causes the air flow to converge and form a single directed airjet 58 that may be both co-axial with the displacement measuring laser beam 13 from the displacement sensor 10 and retain a substantially constant pressure cross section over a working distance range of several inches. The used of an airjet 58 that is coaxial with laser beam 13 generally allows for more consistent results than the use of a single off axis airjet 8.

Referring to FIG. 1, the test is performed during a time sequence controlled by the control computer 30 starting the acquisition of voltage data from the non-contact, pyroelectric temperature sensor 32 which is positioned to receive thermal radiation from sample 3 correlating use to determine the temperature of the sample. Then, the computer 30 opens the electrically activated solenoid valve 26 by way of control line 24 allowing air from the constant pressure source 22 to flow through pipe 6 creating an air jet 8 and impinge on the surface 4 of the binder sample 3, causing the formation of basin 5 with a maximum displacement distance amount 7, which increases over time during the duration of the airjet, against the binder mass restoring force mg. A load cell located underneath and supporting the sample 3 in container 2 is used to measure the force applied to the sample surface 4.

The computer will open or close the solenoid valve 26 to ensure a constant force is exerted by the airjet onto the sample surface. Note that the laser position sensor 10 produces a continuous electronic output signal 11 of the height of the binder surface 4 with respect to a set datum distance within the sensor 10 working distance range. At the beginning of the test, the sensor measured height from the sensor datum is subtracted from the displacement 7 measurements, in effect setting the output height of the surface 4 to zero creating a new datum based on the starting height of the surface 4 of the sample held in container 2. The actual height of the sample 3 surface 4 in container 2 can vary from sample to sample.

When the test begins, the airjet acting on surface 4 of the sample surface starts the downward deformation 5 and the sensor 10 starts to output distance values 7 showing the displacement values from the start position. The distance values in inches or millimeters, may be presented either as positive or negative, however, as the restoring force acting on the sample is gravity and surface is actually deforming downward, we shall use negative distance values and by convention herein, an increasing displacement refers to a negative distance value that is increasingly further from the starting datum.

Commercially available laser based displacement sensors are generally comprised of a laser light source 12 that produces a substantially collimated laser beam 13 that reflects from the surface 4 and is scattered as a diffuse reflection. Some of this light 14 enters lens 16 and is focused onto a linear area of photosensors 18. The position of the focused laser beam spot 17 moves across the photosensor array 18 as the of the surface 4 of the sample 3 deforms 7 causing changes in the signal output 11 of the displacement sensor 10. The output of computer 30 is sent to a computer monitor 34 and displayed either numerically, graphically or both in a manner useful to the operator. Further, the computer program can be designed to provide data useful for evaluating material samples 4. For example, when the solenoid air valve 26 is opened for a programmed period of time 41 as shown on the graph in FIG. 2, the displacement is increasing. With the same air pressure and force from the constant pressure source 22, is applied for the same time period 41, the maximum displacement 7 of the sample 4 is shown as 46 for sample 50. At the end of time period 41, the air jet is turned off by deactivating solenoid valve 26.

Samples can be compared by the total maximum displacement measured. Additional comparison data can be used to evaluate samples such as the determination of the percentage of recover over a set period of time 42, such as 120 seconds after cessation of the air flow (8 and 58). For sample test run 50, the percentage of recovery can be calculated as the Maximum deformation (D) 46 minus the Final Displacement, R, after recovery for a set period of time, 120 seconds, 48, divided by the maximum deformation 46.

$$\text{Recovery \%} = D-R/D$$

Figure 2:
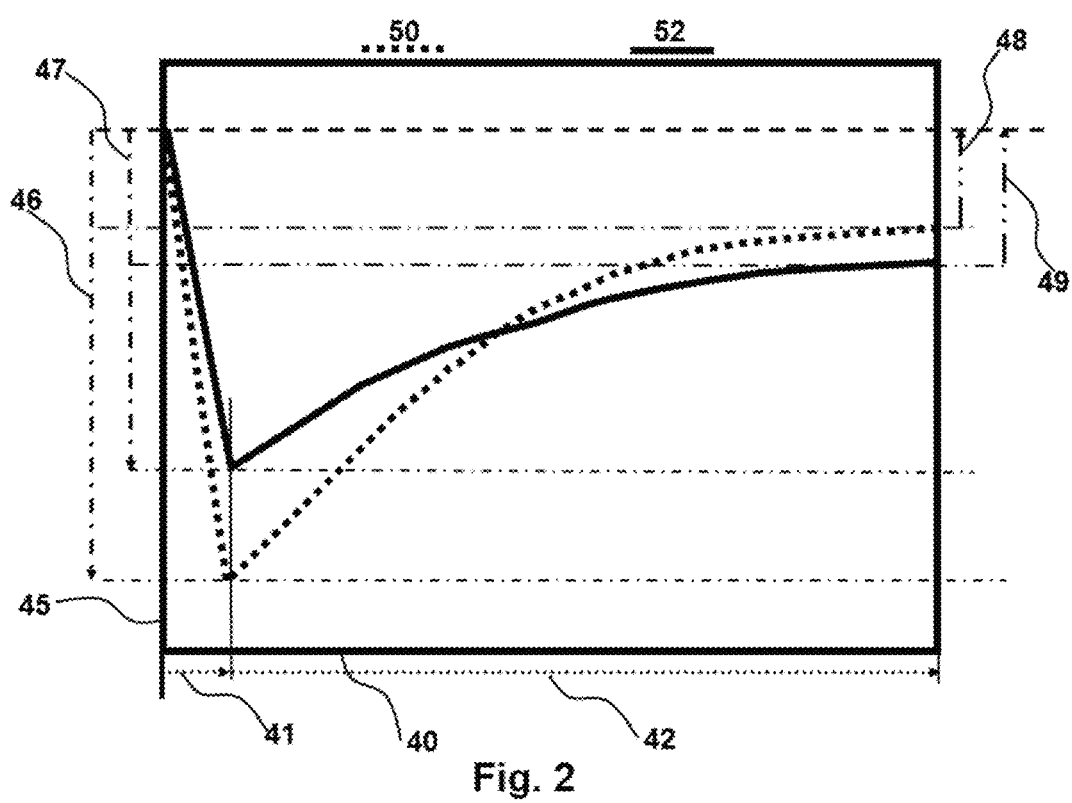
FIG. 2 shows the graphed displacement measurements over time for two samples of non-Newtonian fluids, in these cases asphalt binder.

The two sample tests graphed in FIGS. 2, 50 and 52, for sample 1 and sample 2 respectively, show very different responses. Sample 1, 50, has a larger deformation 46, due to the airjet than does Sample 2, 52 and better recovery 48 compared to 49. Sample 1 has additives in the asphalt binder, Sample 2 does not. For QC applications, base-line tests would be run on material samples. Then production tests would be run on new material to ensure the same results are obtained. The tolerance for variations can be set by testing material samples 4 with known variations in additive quantity. Algorithms change have tolerance factors requiring sample test results to be within a specified percentage of results for a know sample standard. Properties that can be measured include shear viscosity, viscoelasticity, yield stress and squeeze flow.

Another test includes the determination of viscosity, $\mu$, for a sample where the equation takes the form:

$$\mu = c \times \ln(l/kD)/D^2, \text{ where}$$

D=airjet displacement of sample surface c and k are numerical constants for the system.

The calculation could be formed mathematically, or by using a lookup table that is stored in memory.

FIG. 3 shows how a plurality of air jets 56 can be used to converge and form a single airjet 58 that is substantially coaxial with laser beam 13. Air 51 is supplied at pressure through tube 50 into a ring manifold 52. A plurality of tubes 54, are directed towards the sample surface 4, but converging at a spot located above the sample surface. Flow testing demonstrates the vector forces in the air jets combine to create a single jet, in space, directed towards the sample surface, but in a vector direction that is not aligned with any of the tubes used to create the jet 58. Two tubes 54 can be used, but the airjet formed tends to have an elliptical cross section. Three or four tubes 54 tend to produce a well formed air jet with a good working range of several inches.

FIG. 4 shows an alternative arrangement that advantageously eliminates the tubes 54, by creating a hollow convergent cone of air 57 by applying air flow 51 through tube 50 into a circular manifold 55 machined in a cylindrical body 53 made of a material such as aluminum or plastic. A conical tapering hole 54 is machined through the body 53 to provide air flow 57 through an open orifice 60. A top plate 51 having hole 56 for the transmission of laser beam 13 and an inner cone 59 that channels air 57 into a single convergent air jet 58. Alternatively, these parts may be manufactured by precision castings or 3D printing technology.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method for measuring a property of a non-Newtonian fluid, comprising steps of:
    measuring an initial height of a surface of the non-Newtonian fluid held within a container;
    applying at least one fluid jet to a location on the surface of the non-Newtonian fluid held within the container for a first period of time to form a basin in the non-Newtonian fluid, the surface of the non-Newtonian fluid within the basin being displaced from the measured initial height by a first displacement distance amount, the container being different from an application surface to which the non-Newtonian fluid is finally applied;
    measuring the first displacement distance amount;
    measuring a second displacement distance amount relative to the measured initial height of the surface within the basin after a second period of time; and
    calculating a property of the non-Newtonian fluid based on a comparison of the first and second displacement distance amounts.

2. A method for measuring a property of a non-Newtonian fluid according to claim 1, wherein the step of applying at least one fluid jet to a location on a surface of a non-Newtonian fluid comprises applying a single fluid jet.

3. A method for measuring a property of a non-Newtonian fluid according to claim 1, wherein the step of applying at least one fluid jet to a location on a surface of a non-Newtonian fluid comprises applying a plurality of fluid jets.

4. A method for measuring a property of a non-Newtonian fluid according to claim 3, wherein the plurality of fluid jets are directed to a single location on the surface of the non-Newtonian fluid.

5. A method for measuring a property of a non-Newtonian fluid according to claim 1, wherein the non-Newtonian fluid comprises asphalt.

6. A method for measuring a property of a non-Newtonian fluid according to claim 1, wherein the initial height and the first and second displacement distance amounts are measured using a laser-based displacement sensor.

7. A method for measuring a property of a non-Newtonian fluid according to claim 1, wherein the step calculating is performed by a computer.

8. A method for measuring a property of a non-Newtonian fluid according to claim 1, wherein the second period of time includes at least part of the first period of time in which the fluid jet is being applied.

9. A method for measuring a property of a non-Newtonian fluid according to claim 1, wherein the second period of time includes a period after cessation of the application of the fluid jet.

10. A method for measuring a property of a non-Newtonian fluid according to claim 9, wherein the step of calculating a property of the non-Newtonian fluid comprises calculating the viscosity of the non-Newtonian fluid.

11. A method for measuring a property of a non-Newtonian fluid according to claim 10, wherein the step of calculating the viscosity of the non-Newtonian fluid is performed using the formula: $\mu = c \times \ln(1/kD)/D^2$, where D=airjet displacement of sample surface and c and k are numerical constants for the system.

12. A method for measuring a property of a non-Newtonian fluid according to claim 9, wherein the step of calculating the viscosity of the non-Newtonian fluid further comprises determining a temperature of the of the non-Newtonian fluid.

13. A method for measuring a property of a non-Newtonian fluid according to claim 12, wherein the step of determining the temperature of the non-Newtonian fluid is performed using a non-contact temperature sensor.

14. A method for measuring a property of a non-Newtonian fluid according to claim 1, wherein the step of applying at least one fluid jet to a location on a surface of a non-Newtonian fluid comprises applying an air jet.

15. A system for measuring a property of a non-Newtonian fluid, comprising:
    a container within which the non-Newtonian fluid is placed, the container being different from an application surface to which the non-Newtonian fluid is finally applied;
    a temperature sensor;
    structure for creating a fluid jet for forming a basin in the non-Newtonian fluid by displacing the surface of the non-Newtonian fluid within the basin by a displacement distance amount measured from an original level of the surface;
    a displacement sensor measuring displacement distance amount; and
    a computer configured to calculate a property of the non-Newtonian fluid based on a comparison of an initial measured displacement distance amount of the surface within the basin and a final measured displacement distance amount of the surface within the basin following cessation of impingement of the fluid jet on the surface of the non-Newtonian fluid.

16. A system for measuring a property of a non-Newtonian fluid according to claim 15, wherein the computer is constructed and arranged to control the fluid jet.

17. A system for measuring a property of a non-Newtonian fluid according to claim 15, wherein the temperature sensor is a non-contact temperature sensor.

18. A system for measuring a property of a non-Newtonian fluid according to claim 15, wherein the displacement sensor is laser-based.

19. A system for measuring a property of a non-Newtonian fluid according to claim 15, wherein the structure for creating a fluid jet is constructed and arranged to create more than one fluid jet.

* * * * *